United States Patent
Espenhain

(10) Patent No.: US 8,374,669 B2
(45) Date of Patent: Feb. 12, 2013

(54) NEEDLE ELECTRODE WITH DISPLACEABLE COVER AND METHOD OF USING SAID NEEDLE ELECTRODE

(75) Inventor: Torben Espenhain, Skovlunde (DK)

(73) Assignee: AMBU A/S, Ballerup (DK)

( * ) Notice: Subject to any disclaimer, the term of this patent is extended or adjusted under 35 U.S.C. 154(b) by 1108 days.

(21) Appl. No.: 12/085,766

(22) PCT Filed: Nov. 30, 2006

(86) PCT No.: PCT/DK2006/000674
§ 371 (c)(1),
(2), (4) Date: Jul. 31, 2008

(87) PCT Pub. No.: WO2007/062655
PCT Pub. Date: Jun. 7, 2007

(65) Prior Publication Data
US 2009/0036765 A1   Feb. 5, 2009

Related U.S. Application Data

(60) Provisional application No. 60/741,450, filed on Dec. 2, 2005.

(30) Foreign Application Priority Data

Dec. 2, 2005   (DK) .................................. 2005 01705

(51) Int. Cl.
*A61B 5/0492* (2006.01)
(52) U.S. Cl. .......................... 600/373; 600/372; 600/546
(58) Field of Classification Search .................. 600/372, 600/373, 546; 604/6.05, 6.06, 162, 163, 604/171, 192
See application file for complete search history.

(56) References Cited

U.S. PATENT DOCUMENTS

| | | | |
|---|---|---|---|
| 4,781,692 A * | 11/1988 | Jagger et al. | 604/164.08 |
| 5,170,788 A | 12/1992 | Blumenfeld | |
| 5,256,149 A * | 10/1993 | Banik et al. | 604/164.01 |
| 5,478,348 A * | 12/1995 | Bajada | 606/185 |
| 5,482,038 A | 1/1996 | Ruff | |
| 5,626,577 A * | 5/1997 | Harris | 606/45 |
| 5,693,044 A * | 12/1997 | Cosmescu | 606/42 |
| 5,746,215 A * | 5/1998 | Manjarrez | 600/573 |
| 5,762,626 A | 6/1998 | Lundquist et al. | |
| 5,993,447 A | 11/1999 | Blewett et al. | |
| 6,241,664 B1 | 6/2001 | Carr et al. | |
| 6,564,078 B1 | 5/2003 | Marino et al. | |
| 7,537,594 B2 * | 5/2009 | Sartor | 606/49 |
| 2002/0058937 A1 | 5/2002 | Maltese | |
| 2004/0097819 A1 | 5/2004 | Duarte | |
| 2004/0172115 A1 | 9/2004 | Miazga et al. | |
| 2004/0225286 A1 | 11/2004 | Elliott | |

* cited by examiner

Primary Examiner — Lee S Cohen
Assistant Examiner — Erin M Cardinal
(74) Attorney, Agent, or Firm — Dykema Gossett PLLC

(57) ABSTRACT

A needle electrode (1) comprising a base element (4), a needle element (3) mounted on said base element and connection means (5) for connecting said needle element to external electronic equipment. The needle electrode further comprises a cover element (2) which is displaceable between at least two positions: an "active" position where the tip of the needle element (3) is exposed and a "secure" position where the tip of the needle element (3) is hidden within the cover element (2). In this way, the needle electrode (1) is provided with a shield (2) whereby the needle element (3) can be shielded after use whereby the user of the needle electrode (1) is protected from infection. A method of using a needle electrode (1) is also presented. An adjustable length needle electrode (80) is also presented.

7 Claims, 7 Drawing Sheets

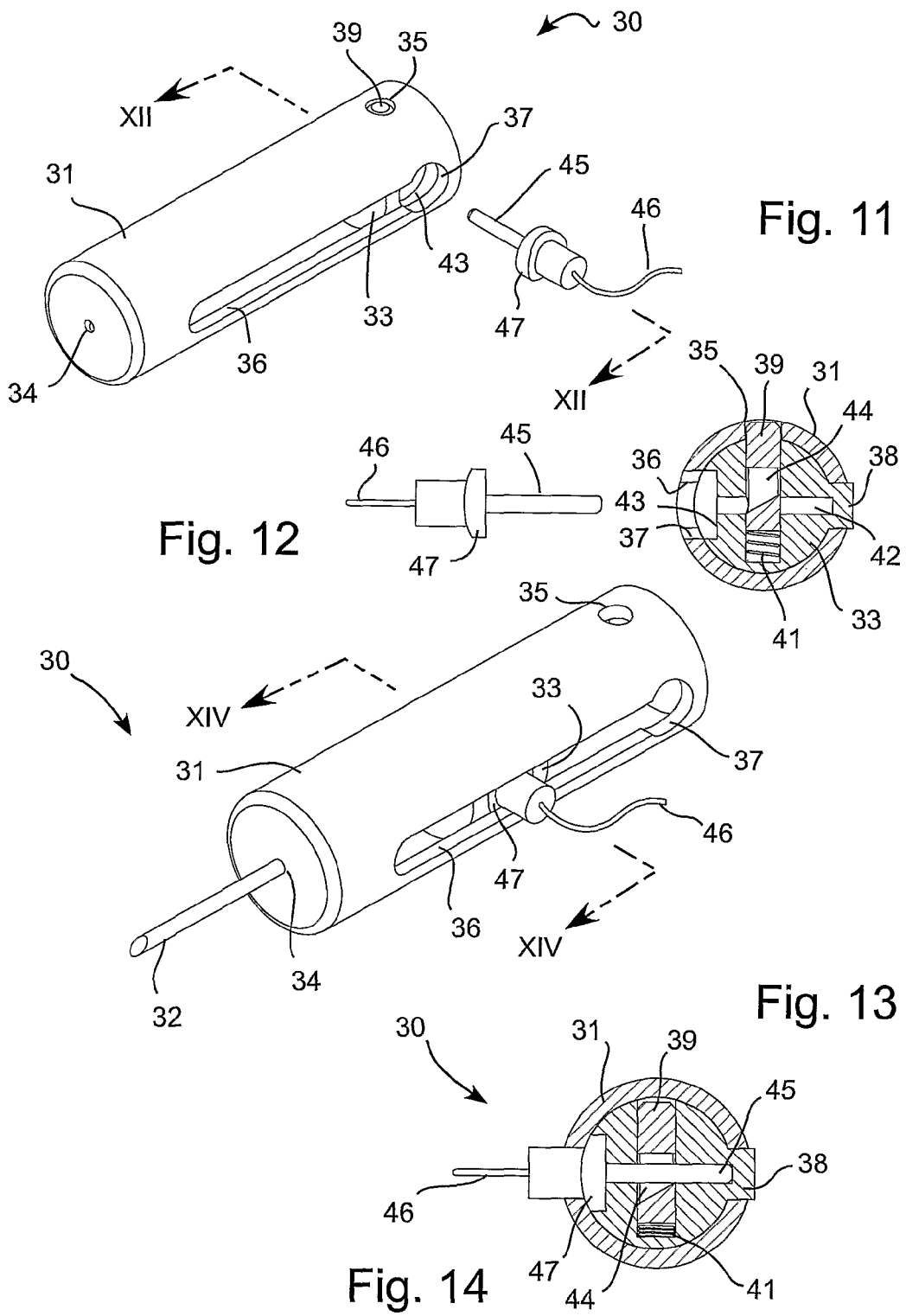

NEEDLE ELECTRODE WITH DISPLACEABLE COVER AND METHOD OF USING SAID NEEDLE ELECTRODE

BACKGROUND OF THE INVENTION

1. Field of the Invention

The current invention relates to a needle electrode including a base element, a needle element mounted on the base element and connection means for connecting the needle element to external electronic equipment. Such needle electrodes are used in many different forms of therapy and/or diagnosis. The current invention also relates to a method of using a needle electrode.

2. The Prior Art

One example of where such a needle electrode is used is for Electromyography (EMG). In this case, the needle electrode is often referred to as an EMG needle electrode. Two examples of currently available EMG needle electrodes are described in more detail in U.S. Pat. No. 6,241,664 and U.S. Pat. No. 5,170,788.

At the start of an EMG procedure, the person performing the procedure, typically a doctor, will unpack a sterilized needle electrode from sterile plastic packaging and connect the needle electrode to external electronic equipment via a wire and a connector. Usually, the external electronic equipment will be used for recording the signals measured by the needle electrode. The external electronic equipment should be known to the person skilled in the art and won't be further discussed here. The doctor will then insert the needle element of the needle electrode into the person's body. After the reading is performed, the doctor removes the needle electrode from the person's body. Typically the doctor performs a number of recordings for each patient. After the doctor is finished with the recordings, the doctor disconnects the needle from the external electronic means and discards the needle electrode.

However, current needle electrodes suffer from a serious shortcoming in that at the end of the procedure, the needle electrode is discarded with no form of safety cover. This means that there is a risk that the person performing the procedure and/or the assisting staff could be pierced by the needle, thereby risking infection.

In addition, during the course of the procedure, the needle part of the needle electrode is often removed from the patient and then re-inserted at a later point in time. During the time that the needle electrode is removed from the patient, the needle part of the needle electrode is fully exposed. There is therefore a risk that the person performing the procedure and/or the assisting staff risk will be pierced by the needle and thereby risk infection.

SUMMARY OF THE INVENTION

A first aspect of the current invention is therefore to provide a needle electrode as mentioned in the opening paragraph where the needle part of the needle electrode can be shielded before being discarded.

A second aspect of the current invention is to provide a needle electrode as mentioned in the opening paragraph which can be shielded and unshielded multiple times.

A third aspect of the current invention is to provide a needle electrode as mentioned in the opening paragraph which has a "passive" safety mechanism, whereby the needle part of the needle electrode is automatically shielded at the end of the procedure.

A fourth aspect of the current invention is to provide a needle electrode as mentioned in the opening paragraph which can be adjusted to different lengths in order to suit different tasks.

The above listed aspects are achieved in part by providing the needle electrode with a cover element which is displaceable between at least two positions: an "active" position where the tip of the needle element is exposed and a "secure" position where the tip of the needle element is hidden within the cover element.

In this way, a needle electrode is provided which can be put into a safe position where the user of the needle electrode is protected from getting pierced by the needle thereby avoiding the risk of infection. Furthermore, since the cover element is displaceable with respect to the needle element, the amount of the needle element which is exposed can be adjusted. In this way, a single size needle electrode can be use for different tasks.

In a preferred embodiment, the cover element can be arranged such that it is repeatedly displaceable between the "active" position and the "secure" position. This allows the user to shield and unshield the needle element numerous times during a procedure.

In one embodiment of the cover element, the cover element can be slideably displaceable with respect to said needle element along an axis parallel to the longitudinal axis of said needle element. These results in a simple mechanism whereby the needle element can be arranged enclosed within the cover element.

In order to provide an even safer needle electrode, the needle electrode can further comprise a safety mechanism which, when engaged, locks the cover element with respect to the needle element in a position where the tip of the needle element is hidden. This safety mechanism can be engaged at the end of the procedure, whereby the needle electrode can be discarded without fear that the needle element will accidentally be exposed. The safety mechanism can furthermore be arranged such that once it is engaged, it permanently locks the cover element in position with respect to the needle element.

In a preferred embodiment of the safety mechanism, the safety mechanism can be arranged such that the safety mechanism engages when the user moves the cover element to a certain position, for example a "locked" position. This makes it very easy for the user to "lock" the needle electrode at the end of the procedure.

In a further embodiment of the safety mechanism, the safety mechanism could be arranged to engage when the external electronic equipment is disconnected from the connection means. In this way, the safety mechanism becomes a passive safety mechanism, not requiring any extra user input other than that which the user would need to perform anyways.

The connection means can furthermore be arranged such that it is disconnectable from said external electronic equipment only when said safety mechanism is engaged. This further increases the safety of the needle electrode, since the user is forced to engage the safety mechanism before the electrode can be decoupled from the external electronic equipment.

In order to provide feedback to the user when the safety mechanism engages, the needle electrode can further comprise signal means. For example, the signal means could emit an audible "click" when the safety mechanism engages. Or the signal means could expose a coloured area on the cover element when the safety mechanism is engaged.

In a simple embodiment, the cover element can be a hollow cylinder with at least one slot arranged in the side of the cylinder along at least a portion of the longitudinal axis of the cylinder. The base element can furthermore be arranged inside the cylinder, and at least one part of the base element can be accessible to the user through the at least one slot. The connection means could furthermore be made accessible through the slot. In this way, the user can easily manipulate the connection means and the base element through the slot in the cover.

In another simple embodiment, the cover element could be a cylinder which is shorter than the needle element and which could be displaceably connected to the base element via a rod and slot arrangement. In this embodiment, only the tip of the needle is covered.

In order to hold the position of the needle element locked with respect to the cover element during the insertion of the needle into the skin of a patient, the needle electrode could further comprise temporary locking means to temporarily lock the position of the cover element with respect to the needle element. This could for example be a push button which the user pushes with a finger and which increases the friction between the needle element and the cover element, thereby preventing the needle element from displacing with respect to the cover while the user applies pressure to the push button.

A needle electrode according to the invention could be used in a method comprising the steps of: connecting the needle electrode to external electronic equipment, displacing the cover element into an "active" position where the tip of the needle element is exposed, inserting the needle element into the skin of an animal or human being, removing the needle element from the skin of the animal or human being, displacing the cover element into a "secure" position where the tip of the needle element is covered, and disconnecting the needle electrode from the external electronic equipment.

The steps, performed between connecting the needle electrode to the electronic equipment and disconnecting the needle electrode from the electronic equipment, can furthermore be performed repeatedly.

The method could also comprise a step at the end of the procedure where the cover element is locked in position with respect to the needle element.

DESCRIPTIONS OF THE DRAWINGS

The invention will now be described in more detail with reference to the accompany drawings. The accompanying drawings show example embodiments of needle electrodes according to the current invention and should be used as examples only and should not be used to limit the scope of the invention.

FIG. 11 shows the third embodiment in a secure position where the tip of the needle element is covered and where the connecting plug has not been connected to the connection means.

FIG. 12 shows a cross section view of the same as defined by the section line XII-XII in FIG. 11.

FIG. 13 shows the third embodiment in an active position where the tip of the needle element is exposed and where the connecting plug has been connected to the connection means.

FIG. 14 shows a cross section view of the same, as defined by the section line XIV-XIV in FIG. 13.

DETAILED DESCRIPTION

Figure 1:
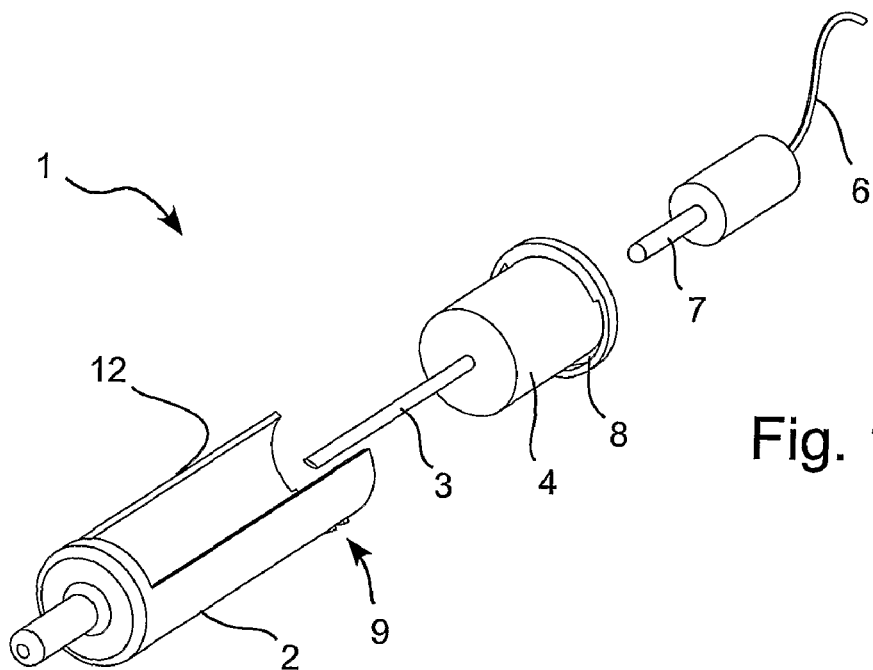
FIG. 1 shows an exploded view of a first embodiment of a needle electrode.

FIGS. 1-7 show different views of a first embodiment 1 of a needle electrode in three different operating positions. The needle electrode comprises a cover element 2, a needle element 3, a base element 4, and connection means 5 for connecting external electronic equipment (not shown). The external electronic equipment (not shown) is connected to the connection means 5 via a wire 6 and a plug 7 at the end of the wire.

The base element 4 is slideably arranged with the cover element 2. The cover element 2 is arranged to pass through the base element via a slot 8 in the base element. In this way, the base element 4 together with the needle element 3 can be displaced within the cover element 2. When the needle element is displaced forward in the cover element, the tip of the needle element 3 is exposed and when the needle element is retracted in the cover element 2, the tip of the needle element 3 is hidden within the cover element. The cover element 2 furthermore comprises a safety mechanism 9 comprising a ramp 10 and a slot 11. The safety mechanism 9 can best be seen in cross section views of FIGS. 3, 5 and 7.

Figure 2:
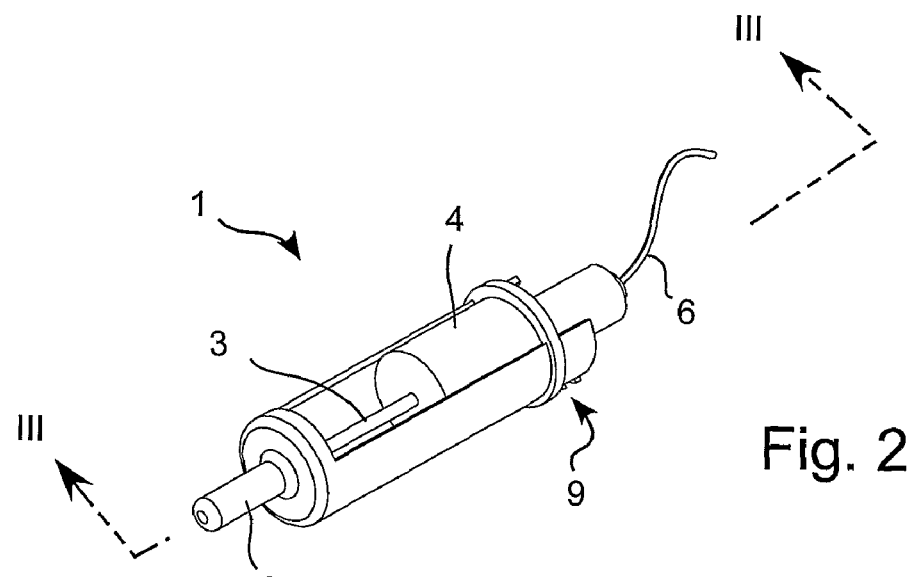
FIG. 2 shows the first embodiment in a first secure position where the tip of the needle element is covered.
Figure 3:
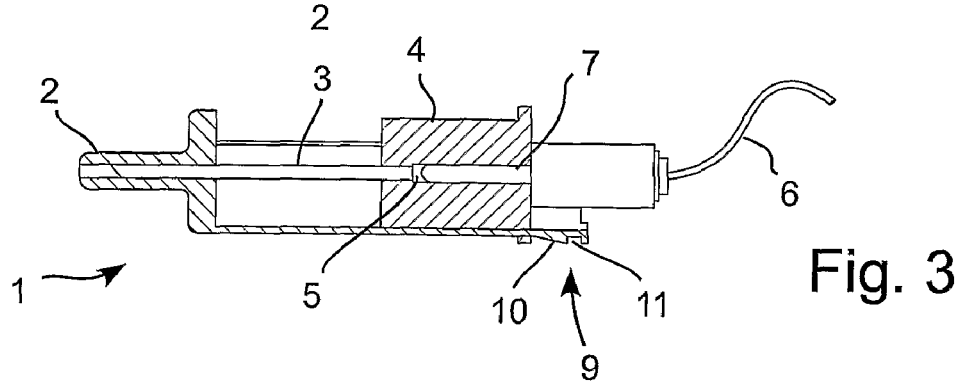
FIG. 3 shows a cross section view of the same as defined by the section line III-III in FIG. 2.

FIGS. 2 and 3 show the needle electrode 1 in a first position. The first position is a "secure" position since the tip of the needle element 3 is hidden within the cover element. This is the position that the electrode is in when it is delivered from the factory. It will typically be packaged in a sterile plastic package. As can be seen, the base element is located in front of the ramp of the safety mechanism and the tip of the needle element 3 is completely hidden. In this position it is not possible for a user to pierce him or herself with the needle.

Figure 4:
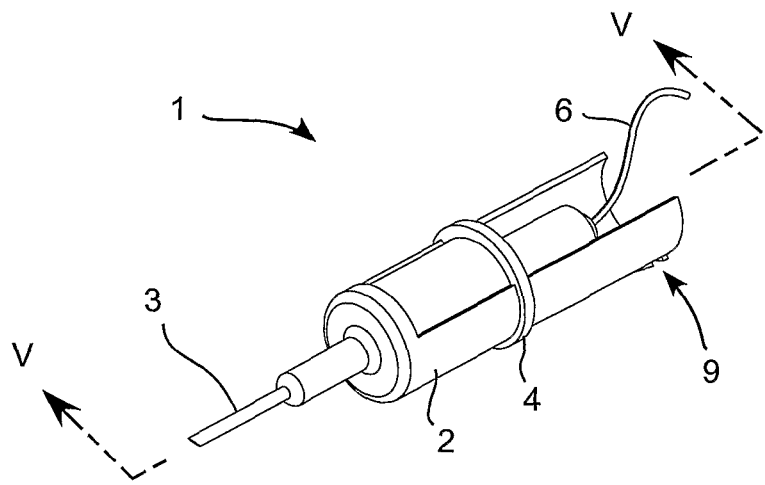
FIG. 4 shows the first embodiment in an active position where the tip of the needle element is exposed.
Figure 5:
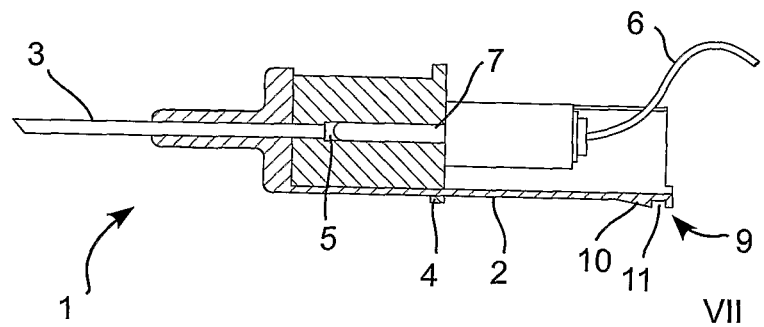
FIG. 5 shows a cross section view of the same as defined by the section line V-V in FIG. 4.
Figure 6:
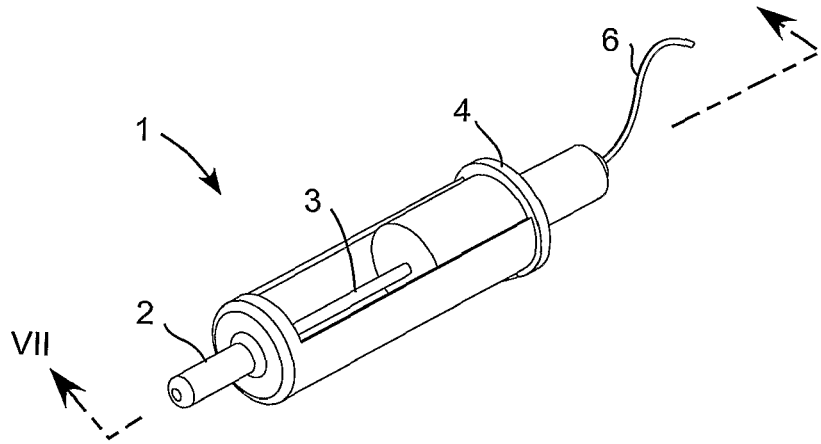
FIG. 6 shows the first embodiment in a locked position where the tip of the needle element is covered and the cover is locked in position with respect to the needle element such that further use of the needle electrode is prevented.
Figure 7:
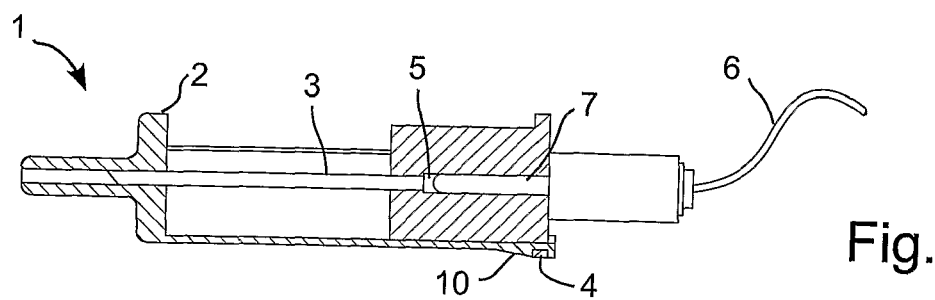
FIG. 7 shows a cross section view of the same as defined by the section line VII-VII in FIG. 6.

FIGS. 4 and 5 show the needle electrode 1 in a second position. The second position is an "active" position. In this position, the base element 4 and the needle element 3 have been displaced forward in the cover element 2 such that the tip of the needle element 3 is exposed. In this position, the needle element 3 can be inserted into the skin of the patient. When the needle is removed from the patient, the base element 4 and the needle element 3 are retracted in the cover element 2 into the "secure" position as shown in FIGS. 2 and 3. During a typical procedure, the needle element 3 and the base element 4 will be moved back and forth between the active position shown in FIGS. 4 and 5 and the secure position shown in FIGS. 2 and 3.

When the procedure is finished, the needle electrode 1 will be discarded. However, before it is discarded, the user retracts the needle element 3 and the base element 4 so far within the cover element that the base element 4 slides up the ramp 10 and engages with the slot 11. This final locked position can be seen in FIGS. 6 and 7. Once the base element 4 has been placed in this position, it is no longer possible to slide the needle element out of the cover element. The connector 7 can then be disconnected and the needle electrode 1 safely discarded.

Figure 8:
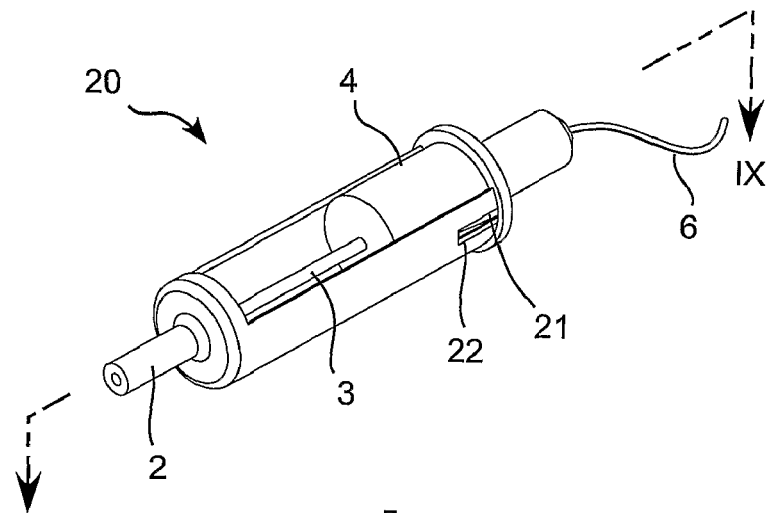
FIG. 8 shows a second embodiment of a needle electrode according to the invention in a secure position where the tip of the needle element is covered.
Figure 9:
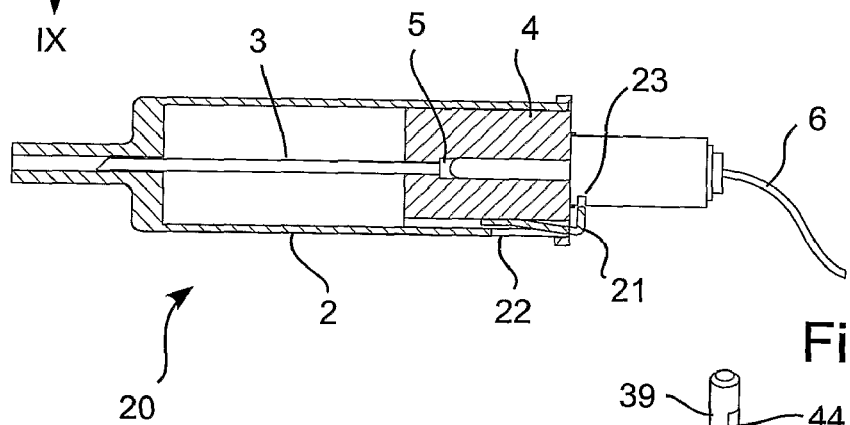
FIG. 9 shows a cross section view of the same as defined by the section line IX-IX in FIG. 8.
Figure 10:
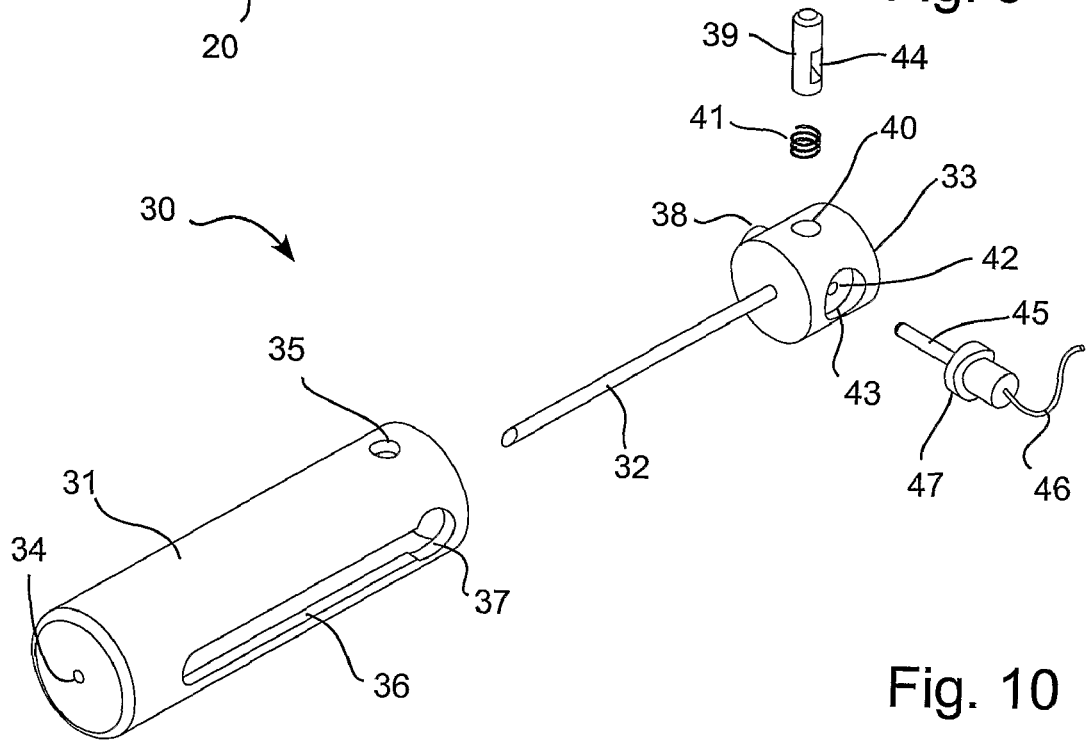
FIG. 10 shows an exploded view of a third embodiment of a needle electrode according to the invention.

FIGS. 8 and 9 show a second embodiment 20 of a needle electrode. In this embodiment, the needle electrode is provided with a spring loaded locking element 21 connected to the side of the base element 4, a slot 22 in the cover element at the end opposite the tip of the needle element 3 and a hole 23 arranged in the body of the connector 7. When the base element 4 is fully retracted, as shown in FIGS. 8 and 9, the spring loaded locking element 21 is arranged in the slot 22 in the cover element 2 and extends outwardly from the base element 4. When the base element 4 is pushed forward in the cover element, the spring loaded locking element 21 comes into contact with the inner side of the cover element 2 and is therefore pressed in towards the base element 4. This causes the end of the spring loaded locking element 21 to engage with the hole 23 in the connector 7. Therefore, as long as the base element 4 is pushed forward in the cover element 2, the connector 7 cannot be removed from the connection means 5.

When the base element 4 is retracted, the spring loaded locking element 21 will again be arranged in the slot 22 and will again protrude away from the base element 4, thereby releasing the hole 23 in the connector. The connector 7 can then be removed from the connection means 5. In this way, the connector 7 can only be removed from the needle electrode 20 when the needle electrode is in its secure position. This is a form of passive security since the user is forced to put the device in it's safe position before being able to remove the connector 7 from the device 20.

It should be obvious to the person skilled in the art, that the features of the first embodiment 1 and the features of the second embodiment 20 could be combined. For example, the safety mechanism 9 of the first embodiment 1 could be added to the second embodiment 20. In this way, the second embodiment 20 of a needle electrode could be permanently locked at the end of the procedure.

FIGS. 10-14 show a third embodiment 30 of a needle electrode according to the invention. The third embodiment 30 comprises a cover element 31 in the form of a hollow cylinder, a needle element 32, and a base element 33. The cover element 31 further comprises needle alignment means 34 arranged at one end of the cover element 31, a hole 35, and a slot 36 arranged on both sides of the cover element 31. The slot 36 on one side of the cover element is furthermore provided with a larger opening 37 at the end of the slot opposite the tip of the needle element 32. The needle alignment means 34 ensure that the needle is held centered with respect to the cover element. This provides support for the needle element, ensuring that it does not bend undesirably.

The base element 33 comprises a protrusion 38 which slideably engages with one of the slots 36 in the cover element 31, a locking pin 39 arranged in a hole 40, a spring 41 arranged between the locking pin 39 and the bottom of the hole 40, connection means 42 and a depression 43. The locking pin 39 is furthermore arranged with a transverse through going hole 44 with a sloping bottom. The external electronic equipment (not shown) is connected to the connection means 42 on the base element 33 via a plug 45 connected to a wire 46. The plug 45 is furthermore formed with a flange 47.

FIGS. 11 and 12 show the needle electrode in a first position. The first position is a "secure position". The needle electrode is in this position when it is delivered from the factory, packed in its sterile packaging. As can be seen from FIGS. 11 and 12, the plug 45 is not connected and the locking pin 39 is biased upwards in the hole 40 by the spring 41. In this position the tip of the locking pin 39 is engaged in the hole 35 in the cover element 31. In this position, the needle element 32 and the base element 33 cannot be displaced within the cover element 31 due to the locking pin 39.

When the user wishes to use the needle electrode 30, the user connects the plug 45 with the connection means 42 in the base element. The user pushes the plug 45 through the enlarged opening 37 in the slot 36 and the flange 47 of the plug 45 is arranged within the depression 43 in the base element 33. Due to the sloped bottom of the transverse through going hole 44 of the locking pin 39, the insertion of the plug 45 in the connection means 42 will force the locking pin 39 downwards in the hole 40, thereby disengaging the tip of the locking pin 39 from the hole 35 in the cover element 31. The user is now free to slide the needle element 32 and the base element 33 with respect to the cover element 31, thereby causing the tip of the needle element 32 to be exposed. The device can now be used actively. This "active" position is shown in FIGS. 13 and 14.

It should be noted that due to the flange 47 on the plug 45, it is not possible for the user to remove the plug 45 from the base element 33 until the user has fully retracted the base element 33 within the cover element 31. This is another form of passive safety mechanism, ensuring that the device is automatically put into its "secure" position at the end of the procedure.

Figure 15:
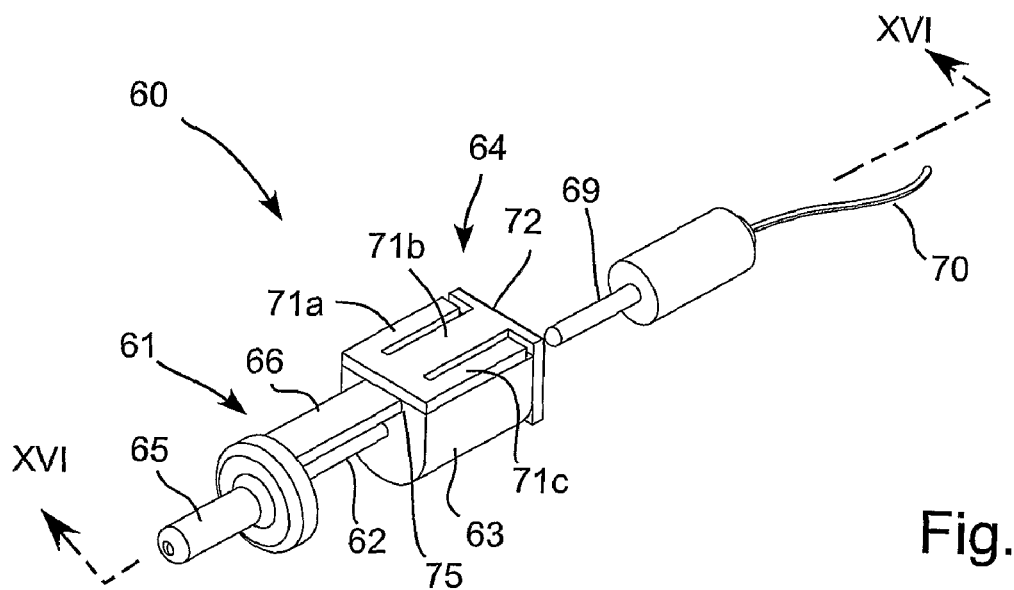
FIG. 15 shows a fourth embodiment in a secure position where the tip of the needle element is covered.
Figure 16:
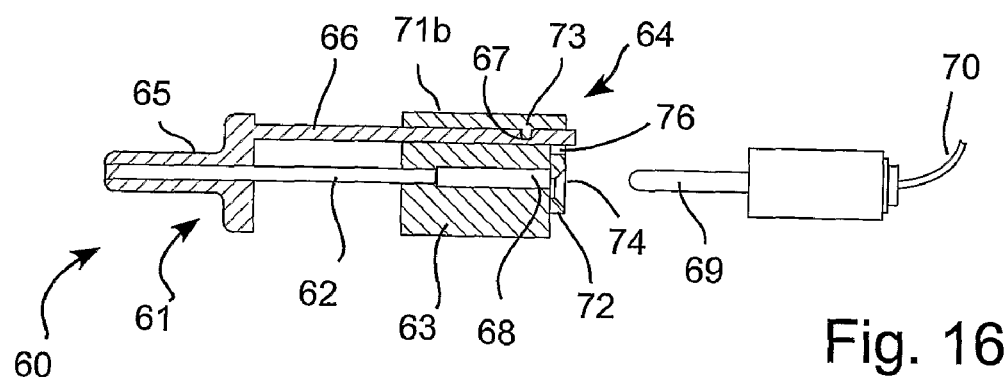
FIG. 16 shows a cross section view of the same, as defined by the section line XVI-XVI in FIG. 15.
Figure 17:
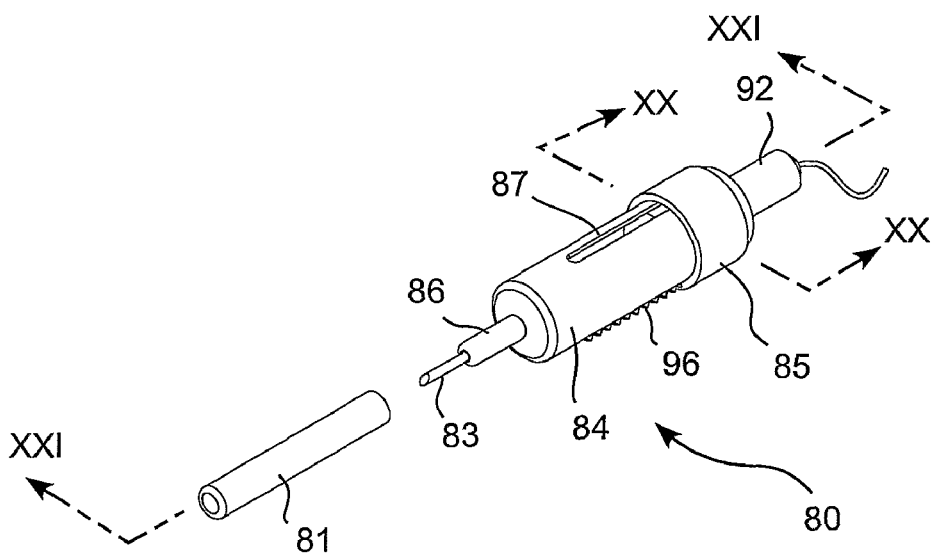
FIG. 17 shows a top perspective view of an embodiment of an adjustable needle electrode according to the invention.
Figure 18:
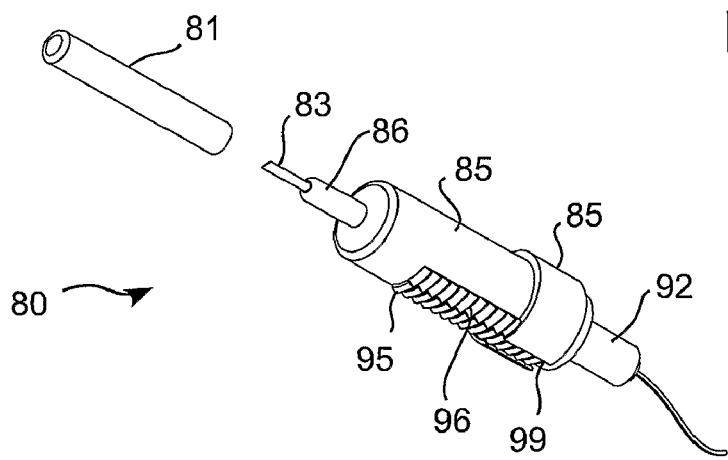
FIG. 18 shows a bottom perspective view of the adjustable needle electrode of FIG. 17 in a first position.
Figure 19:
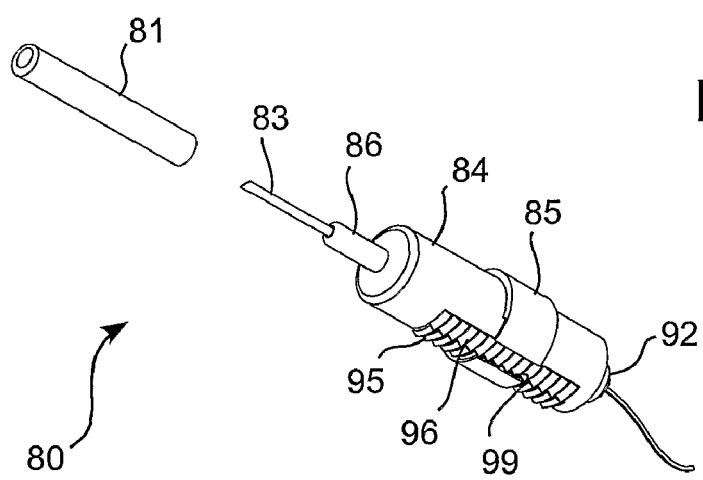
FIG. 19 shows a bottom perspective view of the adjustable needle electrode of FIG. 17 in a second position.
Figure 20:
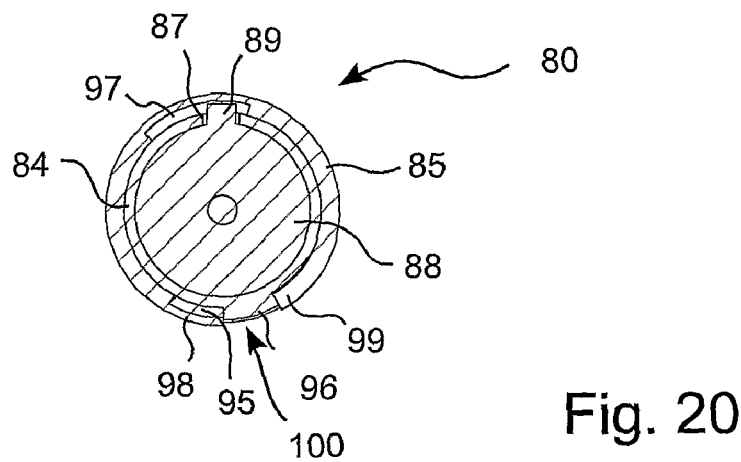
FIG. 20 shows a cross section view of the adjustable needle electrode of FIG. 17 according to the section line XX-XX shown in FIG. 17.
Figure 21:
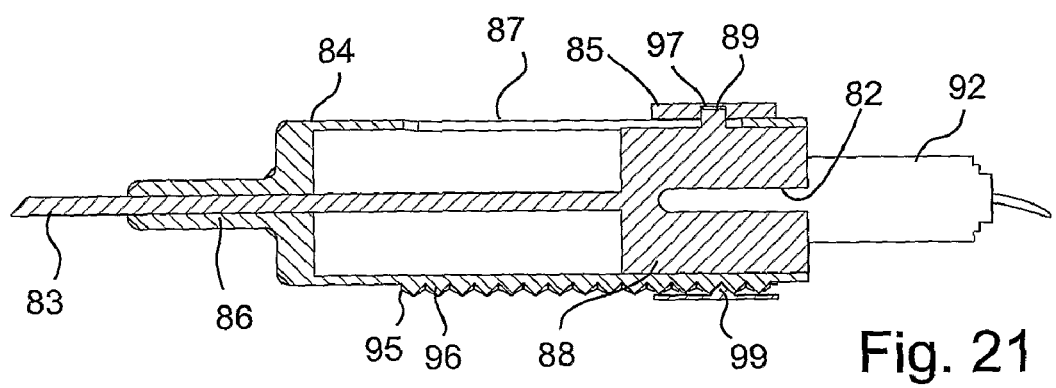
FIG. 21 shows a cross section view of the adjustable needle electrode of FIG. 17 according to the section line XXI-XXI shown in FIG. 17.
Figure 22:
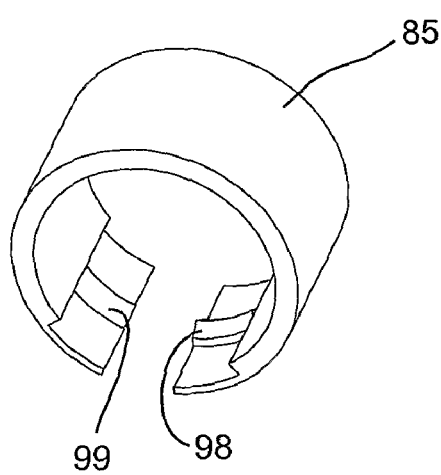
FIG. 22 shows a top perspective view of the locking element of the adjustable needle electrode of FIG. 17.
Figure 23:
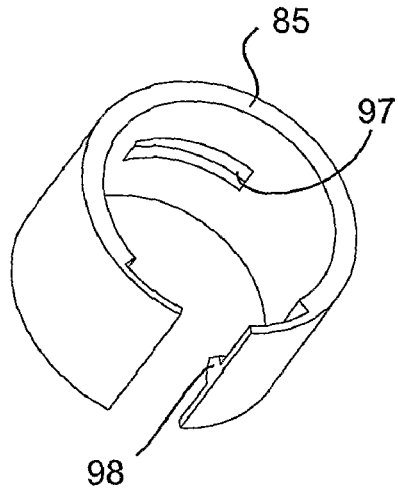
FIG. 23 shows a bottom perspective view of the locking element of the adjustable needle electrode of FIG. 17.

FIGS. 15 and 16 show a fourth embodiment 60 of a needle electrode according to the current invention. The needle electrode comprises a cover element 61, a needle element 62, a base element 63 and a locking element 64. The cover element 61 is comprised of a protection part 65 and a rod part 66. The rod part 66 further comprises a groove 67 arranged in the top surface of the rod part. The base element 63 comprises connection means 68 for connecting a plug 69 whereby an external electronic system (not shown) can be connected via a wire 70. The base element 63 also comprises a groove 75 arranged in its top surface in which the rod 66 of the cover element 61 is slideably arranged.

The locking part 64 is formed with a top surface 71 and a side surface 72. The top surface is split into three sections, 71a, 71b and 71c. The two outermost sections 71a and 71c of the top surface 71 are glued to the base element 63. The middle section 71b of the top surface 71 is flexible and can be bent upwardly and away from the base element 63. A ridge 73 is arranged on the bottom side of the middle section 71b. The side surface 72 is connected to the middle section 71b. The side surface 72 comprises a countersunk hole 74. When the middle section 71b of the top surface 71 is not bent upwards, the countersunk hole 74 is arranged slightly below the centre axis of the connection means 68. In addition, the ridge 73 on the middle section 71b is arranged in the groove 67 in the rod part 65 of the cover element 61. While the ridge 73 is engaged in the groove 67, the cover element 61 is locked in position with respect to the needle element 62.

When the plug 69 is inserted through the countersunk hole 73 and further into the connection means 68, the side surface 72 of the locking part 64 is pushed upwards by the plug 69. This causes the middle section 71b to bend upwards thereby disengaging the ridge 73 from the groove 67. This allows the needle element 62 to be displaced within the cover element 61 and allows the needle element 62 to be exposed. When the user is finished with the needle electrode 60, the user retracts the base element 63 within the cover element 61 and removes the plug. When the plug is removed, the side surface 72 is lowered, thereby causing the middle section 71b to return to its neutral position forcing the ridge 73 into the groove 67 thereby locking the needle element 62 again.

It should be obvious to the person skilled in the art that the above embodiments could all be made from many different suitable materials. Advantageously the main parts could be made as injection moulded plastic parts. Furthermore, it should be obvious to the person skilled in the art, that the embodiment described above are shown schematically and are therefore missing small details. The omission of these details should not affect the person skilled in the art from recognizing the teaching of the current invention.

It should be mentioned that the needle electrodes 1, 20, 30, 60 shown in the figures can be adjusted such that the needle element protrudes different amounts from the cover element. In this way, the same needle electrode can be used for a number of different tasks. In contrast, the currently available EMG needle electrodes are available in a number of different fixed lengths in order to allow the user to select the shortest needle suitable for insertion to a predetermined depth in a muscle under investigation. The reason for choosing the shortest needle is that a long unsupported shank of the needle, between the finger grip and the skin of the patient, bends easily and makes it difficult for the physician to accurately control the position of the needle tip in the muscle. In order to accommodate the range of insertion depths used for EMG procedures, needle electrodes are typically available in lengths of 25 mm, 30 mm, 38 mm and 50 mm. As a result the physician must keep a relative large number of needle electrodes in stock in order to be able to select the right length of needles for particular procedures on patients with variable anatomical dimensions.

FIGS. 17-23 show another embodiment 80 of an adjustable length needle electrode. This embodiment 80 does not have a slideable cover element as did the previously described embodiments. One aspect of this embodiment 80 is to provide a needle electrode as mentioned in the opening paragraph with adjustable free length of the needle to suit different insertion depths with accurate control of the needle tip during insertion. In this way, the needle electrode may be adjusted for different tasks.

Another aspect of this embodiment 80 is to provide an electrode as mentioned in the opening paragraph where the unsupported free length of the needle can be adjusted continuously to any length within its range of adjustment.

Still a further aspect of this embodiment 80 is to provide a needle electrode as mentioned in the opening paragraph where the unsupported free length of the needle can be adjusted in steps within its range of adjustment.

The above listed aspects are achieved in part by providing a needle electrode as mentioned in the opening paragraph with a long needle element mounted on a base element slideably arranged within a stiff support element. The support element has a bushing at one end which guides the shank of the needle element. In this way, the needle shank is supported against bending by the bushing. The support element also has guide means which allow the base element to slide along an axis which is parallel to the axis of the needle element. Due to this construction, the physician is provided with the same control of the needle tip during insertion as with a fixed length needle electrode with the same free length. In order to protect the user of the needle electrode 80, the needle electrode can further comprise a removable protective sheath covering the free length of the needle element in its shortest position. Means for locking the base element to the sliding support element may also be provided to keep the adjusted length stable during use.

The embodiment 80 shown in FIGS. 17-23 comprises a needle element 83 connected to a base element 88, a stiff sliding support element 84 and connection means 82 for connecting external electronic equipment. In the embodiment shown, a plug 92 is connected to the connection means 82. The needle element 83, protrudes through a guide bushing 86 at the end of the sliding support element 84. The free end of the needle element 83 is protected by a detachable sheath 81, which covers the tip of the needle during storage, handling prior to use and when discarding the needle after use.

The base element 88, is slideably arranged within the support element 84, which partly surrounds the circumference of the base element to keep its movement aligned with the longitudinal axis of the needle element. A guide bushing 86, is attached to one end of the support element 84, and provides a sliding fit with the needle shank. The guide bushing 86, supports the shank of the needle element 83 at different positions.

A peg 89 is attached perpendicular to one side of the base element 88 and extends through a slot 87 arranged along one side of the support element 84. An adjustment ring element 85, made from a material with spring characteristics, fits partly around the circumference of the outside surface of the support element. It includes an angular slot 97, which engages with the peg 89 to interlock the axial movement of the ring element 85 with the axial movement of the base element 88. The angular slot 97, allows the ring element to be turned a certain angle in the plane perpendicular to the needle axis.

The ring element 85 further includes a first tooth 98 and a second tooth 99 arranged on the inside surface of the ring element and near a slit 100 in the ring element, the slit 100 being placed opposite the angular slot 97. In the preferred embodiment, a first row of teeth 95 and a second row of teeth 96 are arranged axially on the outside surface of the support element 84. The teeth are arranged such that the first tooth 98 of the ring element 85 engages with the first row of teeth 95 when the ring element 85 is turned to a first angular position of the slot 97 and the second tooth 99 of the ring element engages with the second row of teeth 96, when the ring element is turned to a second angular position. The profile angles of the first tooth 98 and the first set of teeth 95 are large enough (typically larger than 45 degrees) to allow the ring element to be moved with a clicking resistance along the support element 84, but at the same time small enough to ensure alignment of the second tooth 99 with the second row of teeth 96 when the movement is stopped. The profile angles of the second tooth 99 and the second set of teeth 96 is small enough to prevent axial movement of the ring element when the teeth are engaged by turning the ring to its second angular position, thereby locking the needle in the selected position.

This embodiment 80 will allow the physician to grip the needle electrode anywhere on the support element during insertion of the needle to obtain accurate control of the needle tip during insertion.

The above described embodiment 80, was just one example of an adjustable length electrode. However, many other forms of adjustable length electrodes could also be imagined. For example, the locking element in the above embodiment relied on the interlocking of two sets of teeth. In another embodiment, the locking element could rely on increasing the friction between the base element and the supporting element in order to lock the position of the needle element in the supporting element. In another example, the base element and the support element could be connected by a screw thread, whereby the length of the exposed needle element is adjusted by rotating the base element with respect to the supporting element.

It should be obvious to the person skilled in the art that many different embodiments of a needle electrode according to the invention could be provided. Therefore, the scope of the invention should not be limited to the embodiments described above.

For example, the above needle electrodes were all provided with a sliding interface between the base element and the cover element. In another example embodiment, the cover element could be pivotably connected to the base element and pivoted between an active position and a secure position. In a further embodiment, the cover element and the needle element could be arranged like a lipstick mechanism. In this way, the user could rotate the base of the cover element, thereby causing the needle electrode to be exposed.

Furthermore, it should be noted that all the embodiments shown in the figures have been comprised of elements having cross sections which are generally circular. However, the person skilled in the art should see that elements having non-circular cross sections could also be used. For example, a cylindrical cover element having a square cross section could also be used. In this respect it should be mentioned that the term hollow cylinder should be interpreted in the broadest sense of the definition and not limited to cylinders with circular cross sections.

It should also be obvious to the person skilled in the art, that the connection means could take many forms. In the above examples, the connection means are a socket on the base element which can be coupled to a plug on the end of a wire connected to the external electronic equipment. However, the connection means could just as well be a plug on the end of the base element which connects with a socket on the end of a wire. Furthermore, other forms of connection, such as wireless, via a Bluetooth network for example, could also be imagined.

The invention claimed is:

1. A needle electrode comprising
a base element,
a needle element mounted on said base element,
connection means for connecting said needle electrode to external electronic equipment, and
a cover element which is displaceable between at least two positions: an "active" position where the tip of the needle element is exposed and a "secure" position where the tip of the needle element is hidden within the cover element, wherein the needle electrode has at least two different active positions where different lengths of the needle are exposed, and the needle electrode is arranged such that the needle element, due to frictional or locking engagement between the base element and the cover element, is prevented from displacing from any of its positions with respect to the cover element during insertion of the needle into a patient's skin, wherein the cover element comprises a hollow cylinder with at least one slot arranged in the side of the cylinder along at least a portion of a longitudinal axis of the cylinder, wherein the base element is arranged inside the cylinder, and wherein the connection means are accessible through said slot.

2. A needle electrode according to claim 1, wherein said cover element is repeatedly displaceable between said "active" position and said "secure" position.

3. A needle electrode according to claim 1, wherein said cover element is slideably displaceable with respect to said needle element along an axis parallel to the longitudinal axis of said needle element.

4. A needle electrode according to claim 1, wherein said needle electrode further comprises a safety mechanism which, when engaged, locks the cover element with respect to the needle element in a position where the tip of the needle element is hidden.

5. A needle electrode according to claim 4, wherein said safety mechanism engages when said connection means is disconnected from said external electronic equipment.

6. A needle electrode according to claim 1, wherein said needle electrode further comprises signal means which signal to a user when the cover element is moved to its "secure" position.

7. A needle electrode according to claim 6, wherein said signal means are means which emit a click sound when said cover element is moved to its "secure" position.

* * * * *

UNITED STATES PATENT AND TRADEMARK OFFICE
CERTIFICATE OF CORRECTION

PATENT NO. : 8,374,669 B2  
APPLICATION NO. : 12/085766  
DATED : February 12, 2013  
INVENTOR(S) : Torben Espenhain Page 1 of 1

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1167 days.

Signed and Sealed this

First Day of September, 2015

Michelle K. Lee
*Director of the United States Patent and Trademark Office*